(12) United States Patent
Beesley (10) Patent No.: US 7,557,917 B1
(45) Date of Patent: Jul. 7, 2009

(54) SYSTEM AND METHOD FOR ANALYSIS OF GEMSTONES

(75) Inventor: Casper Beesley, Mt. Vernon, NY (US)

(73) Assignee: Collectors Universe, Inc., Santa Ana, CA (US)

( * ) Notice: Subject to any disclaimer, the term of this patent is extended or adjusted under 35 U.S.C. 154(b) by 0 days.

(21) Appl. No.: 11/124,574

(22) Filed: May 6, 2005

Related U.S. Application Data (60) Provisional application No. 60/570,655, filed on May 13, 2004, provisional application No. 60/569,564, filed on May 10, 2004, provisional application No. 60/569,064, filed on May 8, 2004.

(51) Int. Cl.
*G01J 3/30* (2006.01)
(52) U.S. Cl. .................................... 356/318
(58) Field of Classification Search ............. 356/30, 356/326, 318, 369, 317; 700/2, 19, 21, 87, 700/96; 219/121.68, 121.69
See application file for complete search history.

(56) References Cited

U.S. PATENT DOCUMENTS

| | | | | |
|---|---|---|---|---|
| 5,946,089 | A * | 8/1999 | Duer | 356/318 |
| 6,008,896 | A * | 12/1999 | Sabsabi et al. | 356/318 |
| 6,008,897 | A * | 12/1999 | Sabsabi et al. | 356/318 |
| 6,239,867 | B1 * | 5/2001 | Aggarwal | 356/30 |
| 6,515,738 | B1 * | 2/2003 | Barres et al. | 356/30 |
| 7,001,038 | B2 * | 2/2006 | Bock et al. | 362/125 |
| 2004/0183018 | A1 * | 9/2004 | Zhou et al. | 250/341.1 |

OTHER PUBLICATIONS

Internet Achive Wayback Machine, Search results for Jan. 1, 1996-Sep. 7, 2008.*

SSEF Swiss Gemmological Institute, Unified AGTA/GIA/Gubelin/SSEF disclosure policy for the new corundum treatment coming out of Thailand.*
SSEF Facett, International Issue No. 11, Jan. 2004.*
Themelis, "Beryllium-Treated Rubies & Sapphires".
Themelis, "Flux-Enhanced Rubies & Sapphires".
Periodic Table Atomic Properties of the Elements.
Thompson, "Building "Be"-tter? Sapphires".
Search for laser induced breakdown spectroscopy, www.overture.com/d/search/p/netzero/?Keywords=laser+induced+spectr....
Be beryllium (French: glucinium).
New Text Documents.
"Recent Developments in Instrumentation for Induced Breakdown Spectroscopy", www.dekker.com/servlet/product/DOI/101081ASR120004896.
American Gemological Laboratories, Gem Identification Report, Doc. No. ID 13458.

(Continued)

*Primary Examiner*—Tarifur R. Chowdhury
*Assistant Examiner*—Isiaka O Akanbi
(74) *Attorney, Agent, or Firm*—Thomas I. Rozsa (57) ABSTRACT

A system for analyzing the chemical composition of a sample, comprising exciting a portion of the sample to generate atomic spectral emissions; a spectrometer for determining atomic emission characteristics; processor for receiving an output from the spectrometer, analyzing said output to determine atomic composition, said processor predicting at least one of (i) an origin of the sample, (ii) a treatment applied to said sample, (iii) a composition of the sample, and (iv) a feedback signal for controlling a process. Calibration samples are also provided for standardizing readings from the spectrometer.

22 Claims, 1 Drawing Sheet

OTHER PUBLICATIONS

American Gemological Laboratories, Colored Stone Grading Report, Doc. No. CS 36463.
American Gemological Laboratories, Colored Stone Orgin Report, Doc. No. CS 36600.
American Gemological Laboratories, Colored Stone Orgin Report, Doc. No. CS 36762.
Spinel.
"Lab develops colorful beryllium detection technology", chemicals.wycn.net/images/dhaq.gif.
Peretti, et al., "Contributions to Gemology", No. 1 May 2002, www.gemresearch.ch/journal/cover.htm.
Gilchrist, et al., "Spectroscopy: Mastering the Techniques".
Inductively Coupled Plasma-Mass Spectrometry (ICP-MS), Links for Mineralogists, www.uni-wuerzburg.de/mineralogic/links/tools/icp-ms.html.
Chemical fingerprinting of some East African gem rubies by Laser Ablation ICP-MS.
"Inductively Coupled Plasma Mass Spectrometry", www.soes.soton.ac.uk/research/groups/IGU/Icpms.htm.
"Non destructive" Laser Ablation ICP-MS Investigations on Sapphires, ETH.
"Chemical Identification Charts for Beryllium Treated Corundum", GRS.
Test runs ICP/AES OES Spectro Analytical Instruments, Inc.
"Evaluation of gemstones by laser ablation—ICP-AES".
2004 Winter Conference on Plasma Spectrochemistry.
Basic Overview of ICP-AES, www-odp.tamu.edu/publications/tnotes/tn29/technot2.htm.
Spectro X-Lab X-L_engl.ppt.
Spectro Ciros State of the Art CCD-ICP Technology for High Effciency Analysis brochure.
"Secondary Ion Mass Spectrometry (SIMS)", www.mri.psu.edu/mcl/techniques.sims.asp.
"The Sputtering process", www.cascade.co.uk/thesims.htm.
Desktop Mini SIMS, www.microphotonics.com/SIMS.html.
An Introduction to Laser-Induced Breakdown Spectroscopy, LIBS Technique.
The LIBS Technique, pearl1.Ian1.gov/external/LIBS/technique.htm.
LIBS2000+ Laser-induced Breakdown Spectrometer.
Mattley, "Broadband LIBS Analysis of Related Bacillus Spores", Atomic Spectroscopy, Feb. 2004.
Laser-Induced Breakdown Spectroscopy (LIBS), www.imi.cnrc-nrc.gc.ca/english/HTML/Carrefour_d_informations/Factsheets/LIBS.htm.
LIBS2000+ Broadband Spectrometer, www.oceanoptics.com/Products/LIBS.asp.
PORTA-LIBS 2000, Introducing the first truly portable Laser Induced Breakdown Spectroscopy System, kigre.com/scientific.html.
Koenig, "Unique Solid-State Triple Wavelength Laser Ablation System for High Performance Analysis of Solids".
High Peak Power Compact Permanently Aligned MK-367 Nd:YAG Laser System for a Range of OEM Applications.
EX5 Mini Excmer, GAM Laser, Inc.
SpectronMini-Q Series Lamp Pumped Pulsed Nd:YAG Lasers, translate.google.com/translate?hl=en&sl=it&u=www.gsilumonics.com/product.
Hughes, "LIBS-A new beryllium testing method", www.palagems.com/beryllium_libs_testing.htm.
"Laser Induced Plasma Spectroscopy", www.ws.chemie.tu-muenchen.de/laser/LIPS.htm.
Pittcon 2004 Abstracts 17800-400, 17800-500, 17800-600.
www.cascade.co.uk/serv01.htm.
www.sims.asu.edu/funds.html.
www.chem.gmw.ac.uk/surfaces/scc/scat5_5.htm.
fate.clu-in.org/graphite_main.asp.
www.mee-inc.com/sims.html.
www.yb.gmm.gu.se/method.php?ID=5.
kigre.com/MK367data.pdf.
www.quantel.fr/uk/scien/cfr.htm.
www.bigskylaser.com/compactseries.html.

* cited by examiner

FIG. 1

SYSTEM AND METHOD FOR ANALYSIS OF GEMSTONES

REFERENCE TO RELATED APPLICATIONS

The present application claims benefit of priority from, and incorporates by reference in their entirety, U.S. Provisional Patent Application Nos. 60/570,655 (May 13, 2004), 60/569,564 (May 10, 2004), and 60/569,064 (May 8, 2004).

FIELD OF THE INVENTION

The present invention relates to the fields of systems and methods for chemical analysis of gemstones, minerals, geological, oceanographic, meteorological, environmental, biological, forensic, art, and archeological samples, and more particularly to systems and methods for determining the existence and amount of trace elements.

BACKGROUND

There are a number of applications for trace element analysis. Typically, low parts-per-million analysis requires a traditional laboratory environment, and thus cannot be conducted in the field. The laboratory equipment used is relatively large and expensive, and is run by trained technicians.

One application for trace element analysis is gemology, and in particular the detection of characteristics of stones. The Determination of country of origin and treatments and/or enhancements of gemstones has had a profound affect on the value of gem materials. The origin of a stone may be determined based on several significant factors that are fundamentally determined by the geo-chemical environment in which the minerals and/or gems are created. Variations in chemistry, temperature and pressure all affect the structure of the final crystals produced, which serve as a "signature" for a particular geographic area. Changes in these critical components will yield changes in elemental chemistry, physical and/or optical properties and internal characteristics, e.g., secondary micro minerals, which are entrapped in the host crystal during the growth process. Isolating patterns and small changes in optical, physical, elemental characteristics and inclusions commonly provide diagnostic tools for country of origin and enhancement determinations.

Historically, the application of heat to various materials alters the appearance of the gemstones, which when judiciously applied, improve their desirability and salability. These changes can have a significant affect on the value of a gemstone. In the early to mid 1960s, more sophisticated heat treatment procedures were developed to achieve more radical alterations in appearance and in subsequent value. High temperature heat treatment has had a significant impact on the gem market, as well as, the detection of country of origin. Recently, light elements have been added to the heating process along with various fluxes, to produce even more drastic changes in color and appearance. This process has further complicated the detection of origin and the separation of natural from artificially altered or colored gem material.

Because of the nature of the gem market, stones which have been treated are generally worth less than corresponding untreated stones which have a similar appearance, due to the relative rarity of the untreated stone. There is therefore an incentive to try to pass off treated stones as untreated stones, to develop new and more difficult to detect treatments, and methods of determining whether a stone has been treated. It is also useful to determine an origin of a stone, since this may also influence its value, and help distinguish whether a treatment has taken place to alter a characteristic of the stone.

Detection of these three critical value-related gem treatments/enhancements have been via microscopic, spectral and elemental techniques, that examine physical, optical and chemical characteristics of the stone. However, to date, each method has demonstrated significant shortfalls in one or more of reliability, efficiency and cost per analysis.

Microscopic techniques require a high level individual of experience and expertise, as well as, requiring a substantial and reliable sample set and a thorough familiarity of characteristics associated with particular origin. In addition, the observer must be familiar with the impact of high temperature alteration and various properties and internal characteristics. Microscopic techniques are typically non-destructive.

Spectral characteristics can also be useful diagnostic tools to determine both origin and heat alteration. Spectral techniques are also typically non-destructive.

The most complex of these three techniques is the elemental analysis. Except for spectral techniques, which have insufficient sensitivity for distinguishing the various origins and treatments, elemental techniques are quasi-non-destructive. That is, while removal of a physical sample of the specimen is required, the sample is small, and the remaining portion of the stone is typically available for its intended purpose without substantial impairment of value, and indeed, as a result of the test, may have an increase in value. The particular challenge addressed by this technique is the detection of the addition of light elements, which have the ability to radically alter appearance, and potentially the value of the stone. These light elements include, for example, Beryllium (Be), Lithium (Li), Magnesium (Mg) and Potassium (K), which are added to the flux environments in which the gems are heated. Penetration of a treatment can vary in depth from near surface to throughout the entire stone. The flux itself is part of a treatment which serves to fill cracks and voids in the stone, potentially improving optical clarity.

To date, SIMS (Secondary Ion Mass Spec) has been used to determine elevated levels of Beryllium and related elements. SIMS is expensive, complicated and requires a high level of expertise to operate and interpret data.

ICP-MS (Inductively Coupled Plasma Mass Spectrometry) has also been successfully used to accomplish detection of these light elements. However, its high maintenance cost, coupled with complexity, limits the population of potential users.

LA-ICP/AES-OES (Laser Ablation Inductively Coupled Plasma Atomic Emission Spectrometry-Optical Emission Spectrometry) is a viable laboratory option, which typically employs a non-portable laser ablation system, and has a short sampling time, while maintenance and complexity of use are within the capacity with a reasonably skilled technician.

Laser Induced Breakdown Spectroscopy (LIBS) is known as a good candidate for in situ chemical analysis of geological specimens, since the technique can be performed on a small sample with little or no preparation. It provides a multielement analysis coupled with good sensitivity, very high spatial resolution, and depth profiling capability.

LIBS is also known as Laser Spark Spectroscopy (LASS), and Laser-Induced Plasma Spectroscopy (LIPS). LIBS is a form of atomic emission spectroscopy in which a pulsed laser is used as the excitation source. The output of a pulsed laser, such as a Q-switched Nd:YAG, is focused onto the surface of the material to be analyzed. For the duration of the laser pulse, which is typically 10 nanoseconds, a very high power density is present at the surface of the material. For example, the power density in excess of 1 Gigawatt/$cm^2$ is possible using only a compact laser device and simple focusing lenses. A small amount of material from the surface of the material to be analyzed is vaporized from the surface by a process known as laser ablation, and the dielectric breakdown of the medium by the focused laser energy excitation near the point of ablation causes a short-lived but highly luminous plasma with instantaneous temperatures reaching 10,000° C., and supersonic expansion. A portion of the ablated material forms part of this plasma, which includes highly ionized atoms. After the laser pulse subsides, the expanding plasma cools. During this time the excited ions and atoms emit characteristic optical radiation, unmasked by the laser excitation and plasma emission themselves, as the atoms drop to lower energy states and recapture electrons. A time-gated spectral analysis of this radiation yields information on the elemental composition of the sampled material. By selecting gate timing, atoms having similar bandgaps, but differing characteristic recapture time-constants, can be distinguished, and the effects of the excitation pulse itself minimized. Such gate delays may be from 1-50 microseconds.

Since the initial sample is small, and the laser ablates the material near the focal point, sequential samples allow a depth-sensitive analysis. Because the technique does not require a collection of the sample into a protected sample space, LIBS can be performed remotely. Likewise, the laser itself may be used to clean the sample surface prior to analysis.

The LIBS instrument may be calibrated to perform quantitative measurements of minor elements within a matrix material. Known examples include chromium in steel, magnesium in aluminum alloy, iron in glass, copper in copper sulphate solutions. Calibration may be achieved using matrix-matched certified reference materials containing various amounts of the analyte to be measured. Without controlling for the matrix composition, the technique can only be semi-quantitative, since the amount of ablation and fractionation effects are difficult to accurately predict. An internal standardization may also be performed, by quantifying the analyte of interest and the bulk matrix components, and determining a ratio; however, where the analyze may be 5-6 orders of magnitude below the bulk matrix, such methods may introduce substantial errors. On the other hand, such internal standardization may be used in conjunction with external standards to correct for potential variability and imprecision in the system itself. Internal standardization may also be applied to a plurality of analytes, yielding relative quantities within the bulk matrix.

In many cases, only one laser pulse is needed to analyze a material, allowing a large number of samples to be rapidly identified. On the other hand, the application of a double (or multiple) pulses on the sample surface or intersecting the plume at a different angle (e.g., 90° to the initial pulse) is also known, resulting in observed increase of the sensitivity of the technique. The improvement of the double pulse LIBS figures of merit are related to the enhancement of the emission line, increase of contrast and reduction of ignition threshold.

Other applications of trace element analysis include mineralogy, geology, oceanography, meteorology, environmental science, biology, forensic investigation, art materials analysis, and archeology. In each case, the availability of an instrument for field use which would provide quantitative trace element analysis at relatively low cost is lacking.

SUMMARY AND OBJECTS OF THE INVENTION

The present invention employs LIBS (Laser Induced Breakdown Spectroscopy) for sample analysis, which offers, as compared with previously applied techniques, such as SIMS, ICP-MS and LA-ICP/AES-OES, somewhat lowered detection limits, rapid analysis cycles, potential portability and significantly reduced hardware costs, as well as, simplicity of use, to accomplish full spectrum analysis and a broad coverage of the entire elemental spectrum. LIBS is advantageously can be in conjunction with LA-ICP/AES-OES, especially if a common excitation/ablation source (e.g., laser or electron beam), and spectrometer were employed.

The analysis is preferably used to detect trace element levels in a quantitative or semi-quantitative manner, for example to determine ratios of trace elements, ratios of analytes to internal or external references, or the like. This analysis may be useful in a number of fields, especially where results are available quickly and at relatively low cost, such as for analyzing gems to determine origin and the nature of any applied treatments.

In mineralogy and geology, this system and method may be used, for example, detecting rock or mineral composition in the field. In oceanographic studies, analysis of salt residues and sediments, both as a static condition and over time, may be useful. Likewise, in meteorology, precipitation samples may be analyzed for trace elements to track pollution and wind patterns. The techniques also may be used to track environmental pollution and patterns, and offer the possibility of near real time analysis for process feedback and remediation. Biological and agricultural samples may also be analyzed for toxins, country of origin, pathology. Hair, nail and skin analysis may be performed. The techniques may also be used in forensic investigation. Artists materials may be analyzed for technique, composition, authentication, and origin. Archeological samples may be tested to determine conditions and history of use, origin, degradation, or the like. The technology may also be used to analyze petroleum or byproduct composition.

Trace element applications that parallel gemological analysis includes the detection of trace elements and toxic components in sediments, residues and contaminants. Archeological verification of authenticity, origin and treatments are also relevant to this application. Samples such as emeralds retrieved from sunken treasure ships are known to have been diluted with modern examples in order to realize a higher value due to the purported antiquity of the samples in question. Analysis of sea salt consistent with the recovery site deposited in the fractures of authentic emeralds of archeological significance can be verified using the systems and methods according to the present invention, e.g., LIBS, or other technique. This principle can be applied to pollutants in tracking elemental components in both salt and fresh water estuaries. A similar concept can be applied to extensions of trace element body chemistry as derived from hair, nails, teeth and skin samples in order to investigate the presence of body toxins specifically associated with body pathology.

Both LA-ICP/AES-OES and LIBS employ laser ablation applied in its simplest and most efficient form. LIBS, in particular, permits portability, although a portable LA-ICP/AES-OES device is contemplated by the present invention.

Sample tests using various available ICP-MS devices have shown that low ppm trace beryllium concentrations are not consistently detectable.

According to a preferred embodiment of the invention, LIBS and/or LA-ICP/AES-OES technologies are used to analyze geological and gemological specimens, especially to determine trace element composition. Advantageously, there can be integration of the LIBS and LA-ICP/AES-OES instruments, especially through the use of a common laser or even common laser sampling event, use of a common spectrometer, as well as use of common data analysis equipment. Further, the LA-ICP/AES-OES technique may also be enhanced, for example through the use of spectrometer gating delay or an optical shutter, to detect phosphorescent emissions, that is, optical emissions shortly after a broadband emission ceases. For example, a fiber optic feed can be provided in the LA-ICP/AES-OES spectrometer, to make it also available for LIBS spectrometry.

The present invention advantageously employs a 1064 nm laser with an output of 3-500 mJ/S (mW). Thus, the use of a harmonic converter, with its associated cost and reduction in power output, may be avoided. The power may be delivered either to focusing optics or through a fiber to the optics.

In order to enhance absorption at the surface of the sample to be assayed, an absorptive dye or pigment may be placed on the surface. This dye or pigment may be specifically selected or formulated for high absorption at the excitation wavelength, as well as having little or no effect on the results assay itself. On the other hand, the dye or pigment may also be formulated to include an analyte of interest or a reference analyte, to allow quantification. For example, a silver compound or colloidal silver may be present in the composition. This silver is detectable in a LIBS system at levels of less than 1 ppm. The silver would not normally be expected as a natural component of the stone, e.g., corundum, nor as part of an enhancement treatment.

The dye or pigment may be placed on the sample as a thin film, for example with a soft porous applicator, similar to a marker, or as a dip. The film itself is applied under conditions that will result in a consistent thickness, so that a laser pulse will vaporize a standardized amount of the reference analyte.

The instrument may also be calibrated through the use of standardized thin films containing one or more elements, especially those which have optical emission peaks near those of the analytes of interest. The invention therefore encompasses these reference films and their use in calibrating the instrument.

Other likely useful reference analytes include chromium and mercury.

Borax is a fluxing agent commonly used in mineralogical applications. The flux acts as a dissolving agent for powdered minerals via diffusion throughout the medium under elevated temperatures. Historically, borax and other flux materials can be used to detect macro elemental compositions based on a visually detectable change of color in the normally transparent flux bead once it has dissolved on contact, the powdered mineral to be tested. An application of flux in accordance with the present invention provides a controlled contamination high purity borax or other flux agents, in order to allow a pellet or target to be fabricated for qualitative and quantitative standardization, for ablation techniques such as ICP-MS/ICP-OES/AES or LIBS. If necessary these targets of varying concentration can be assembled or fused into a sequence of discrete elements as a continuum of targets that can be used for the calibration of laser ablation devices. Thus, instead of using natural or synthetic mineralogical standards, the flux pellets may provide a suitable and lower cost substitute. In addition, the flux pellets may provide a standardization reference for flux portions of fracture filled samples.

In known manner, a double pulse option significantly increases signal with LIBS, and this is a preferred technique. Double pulse LIBS can be applied in fs (femto second) or ns (nano second) ranges. For example, a 2 ns pulse separation is suitable, although other separations are possible, and may be advantageous under various circumstances. The laser pulses can be split into two or more paths, for example at 90° to each other, with one directly incident on the surface and the other skimming the surface, so that during the second pulse, the skimming beam reexcites the plume without further ablating the surface.

These techniques permit the detection of light elements and heat enhancements/treatments in sapphire and ruby as well as related materials. These light elements are believed to enter the crystalline matrix of the corundum through a process known as "lattice diffusion", and may be uniform or non-homogeneously distributed through the stone. By selecting locations for laser ablation, multiple samples may be obtained, for mapping the distribution of analyte within the sample. Further, the laser may be used to ablate material at differing depths, allowing depth profiling of the sample. An automated mechanism may be provided to select the sample location and sampling conditions.

According to one embodiment of the invention, a stage is provided which facilitates obtaining multiple samples representing a regular spacing or array of locations about the object to be analyzed. For example, an automated stage may rotate a cut stone to allow samples to be taken at regular spacings (e.g., 90 degree intervals) about the girdle (widest diameter of the stone).

Laboratory grown (synthetic from pure or natural geological material origin) and natural gem materials may be separated or distinguished based on trace element analysis, for example paraiba tourmaline and pink beryl. Natural samples tend to have differing trace elements and trace element profiles than synthetic minerals. The natural processes which develop mineral deposits may show distribution variations, which might not be expected in a controlled synthetic process.

In addition, some gemological samples are treated by a process which generates a synthetic or simulated stone material, for example to fill voids or cracks, to coat a gem, or to emulate the appearance of a natural product. One particular issue in gemology is the use of fluxes of dissimilar (e.g., borax) or similar or related chemical composition to the natural mineral, which are used as fracture or cavity filling agents to uncut or preformed minerals to allow greater utilization of the raw material. Likewise, cementing agents may be used to create composites of stone and other materials. The present techniques may therefore be used to analyze various regions of a specimen, to detect inhomogeneity or the existence of such treatments or processes or the specific identity of the flux agent.

V. I. Solomonov, S. G. Mikhailov, A. I. Lipchak, Yu. S. Kozlov, Impurity Luminescence of Alexandrite Crystals, Journal of Applied Spectroscopy, Volume 69, Issue 3, May-June 2002, Pages 423-429, discloses the use of a high current electron beam in the analysis of the luminescence of alexandrite. Alexandrite has bands of the impurity ions $Cr^{3+}$, Cr—Cr pairs, and also a band at $\lambda$=492-495 nm. Thus, electron beam excitation may be used in the analysis of trace elements, especially in minerals. According to the present invention, as an alternate to, or in conjunction with a laser, an electron beam may be used more generally to ablate or excite a sample and generate a plasma for an optical emission spectroscopy technique.

Different mines and geological conditions lead to different growth environments for gemstones. These differences include, for example, temperature, pressure, time, and chemical composition. The methods and apparatus according to the present invention may therefore be used for detection of country (location) of origin of gems, based on trace element analysis. Typically, one might seek to perform analytical profiles for each respective potential source, and then use the profiles as a vector against which to match an unknown sample. Thus, a database is compiled with the various sources as exemplars, and the unknown sample compared with the exemplars. A statistically large sample is desired, demonstrating both mean values of constituents, as well as statistical variability for particular values.

This method, however, relies on standardization or calibration of test results, since in a sample database, the results may be obtained on different equipment, using possibly different methodology, and a different time, and with different adjustments and normalization. To improve results, it may be preferred to employ a physical exemplar or set of exemplars, so that the same system, using the same methods, under the same sampling conditions and calibration, may be used to interpret the data readings from the instrument. The physical samples may be synthetic or natural. Ideally, in a laboratory setting, a putative match is confirmed by comparing the unknown sample with an authenticated sample from the same origin. In field operation, a set of calibration specimens may be provided which encompass a broad range of trace element constituent variations may be used. This set is, for example, a collection of synthetic minerals, or flux impregnated pellets of known impurity composition, which can be designed for optimal use, readily marked for identification, and made available in large quantities of essentially identical kits.

It is also possible to provide one or more calibration specimens which have graded impurities, wherein a sample location on the specimen defines the concentration of one or more trace elements, thus allowing a reduction in the number of sample specimens required, while permitting flexibility in the calibration or normalization process.

In some instances, it may be possible to define algorithmically the effect of a putative treatment on the composition of a stone. That is, given a natural (or synthetic) stone of a certain origin or having certain characteristics, the resulting characteristics after treatment may be predicted. Likewise, given a tested sample having certain characteristics, the origin and treatments applied, if any, may be predicted.

Typically, it is not reasonably possible to start with a natural stone of particular origin, and apply a treatment which will result in a treated stone which so closely resembles a stone of different origin, that it is indistinguishable, especially when using LIBS and LA-ICP/AES-OES, in conjunction with a physical analysis of the stone using traditional gemological laboratory techniques. Thus, while a treatment may sufficiently alter the appearance of a stone such that the traditional techniques are incapable of definitively determining that a treatment was applied, when these stones are further analyzed by LIBS and/or LA-ICP/AES-OES, differences are apparent. For example, the resulting color of a stone may result from one of a number of different factors, only one of which is trace composition of light elements. In fact, the natural processes which produce gemstones involve a variety of factors, some of which are not known to be alterable after formation of the stone. Thus, while the visible appearance may be indistinguishable, the chemical composition is distinct. Likewise, since these other factors are present, seeking to alter the trace element chemical profile of a natural stone through external processes after formation will typically not result in a stone which appears identical to a natural stone without treatment. Thus, the combination of physical and chemical examination of the stone, especially corundum-based minerals, is difficult to deceive.

While to be avoided as a basis for deception or fraud, the chemical composition algorithms may also be used to guide the treatment of particular stones to yield desired effects. That is, by analyzing a stone before treatment, the treatment process may be optimized on the basis of the analysis to yield a superior or more efficient result. The analysis technique may also be used as part of a closed-loop feedback mechanism to control a treatment process.

It is also possible to have a hybrid scheme, employing database lookup, algorithmic interpretation and analysis, and/or physical sample testing, to produce a report or output. Accordingly, it is not necessary for the output of the analytical device to be highly accurate, since various means are available to correct the output. On the other hand, high precision is desirable, since some trace elements are present at levels of 5 ppm or below. Further, treatments may be synergistic, and the treatment technologies ever-evolving, so analytical instruments with limited precision or sensitivity may present an opportunity for circumvention.

Since the device according to the present invention includes a laser suitable for ablating regions of the surface of the gemstone, the laser, during or in conjunction with sampling, may impart a marking on the stone for later identification and authentication. Suitable and adjunct technologies are disclosed in U.S. Pat. No. 5,932,119, which is expressly incorporated herein by reference in its entirety. Likewise, the system according to U.S. Pat. No. 5,932,119 may be modified to incorporate the analytical technologies according to the present invention, especially when applied to non-diamond minerals. Typically, the use of a dye or pigment on the surface of a stone to be analyzed is to be avoided, since this may disrupt the analysis process, although selected dyes or pigments may make the process more efficient, especially of the composition of the dye or pigment is known and controlled to avoid the analytes of particular interest. For example, a relatively pure carbon black or graphite target may be placed on a desired sample location of the stone to efficiently absorb laser irradiation. It is noted that the present technologies may also be applied to diamonds, for example to determine certain treatments or country (mine) of origin.

As discussed above, the composition of gemstones may be depth profiled, especially for surface/bulk (lattice) diffused gem materials. In this case, there is an opportunity for internal control; that is, the fact that a raw or cut gemstone has a surface to center variation in a diffusible analyte may be used to infer that the analyte was recently (on geological terms) treated at its surface with this analyte. Thus, the absolute value of the measurement is not as important as the relative measurements with variations in depth. Further, since such variations at the surface may be exponentially varying (since the causative process is presumed to be principally diffusion), the actual depth required is not great, and therefore the test need not be deemed destructive.

The techniques employed according to the present invention have high sensitivity (in parts per million, ppm) for major, minor and trace elemental components of gemstones. That is, the sensitivity and dynamic range is sufficient to allow determination of the matrix of the stone, in addition to the trace elements therein. For example, one may look at a ratio of a putative exogenous trace element, such as beryllium, as compared to a natural component, such as iron, to determine composition. This alleviates a need for high dynamic ratio comparisons between trace and dominant elements, and further allows efficient comparison of characterizing features without absolute quantification of trace elements. Simultaneous multi-element analysis of sequential laser pulses is achievable in throughputs of samples per second. While typically, the stone mounting process in the apparatus requires manual efforts, the laser pulsing and sample acquisition take microseconds, and the sample repeat rate is limited principally by the laser repetition rate, potentially in the thousands of pulses per second, and the data acquisition rate, which may be hundreds or thousands of samples per second. The settling time for significant (non-adjacent) mechanical repositioning of the laser may allow tens or hundreds of samples per second, if precise placement is not required. Thus, the limiting factor may well be the control system, which must control the process, set up for a sample, trigger the laser, acquire data from the spectrometer, and possibly seek to analyze this data when acquired, and store the raw or processed data, for each sample.

The preferred embodiment includes the following features:
1) Laser power can be adjusted for optimization of elemental response and to avoid excessive damage to the sample.
2) Argon can be used as the carrier gas to purge the general environment.
3) Calibration standards like NIST 610 glass standard and high purity aluminum oxide ($Al_2O_3$) can be used in the quantification process.
4) These procedures can be used to establish origin and color classification, for example:
   a) Sapphire/ruby—iron concentration, iron/chromium relationship, trace elements.
   b) Emerald—iron/chromium/vanadium relationships, trace elements.
   c) Paraiba Tourmaline—Brazil, varying Iron (Fe), Copper (Cu) and Beryllium (Be) concentrations to confirm the nature and the origin of the material.
   d) Pink/Red Beryl—Madagascar, confirmation of Cesium content (as compared to other geographic origins)
5) LA-ICP/AES-OES quantification of elemental composition of a sample relative to a reference standard based on determining which wavelengths and the intensities that are emitted by the sample.
6) Ability to detect elemental concentrations of beryllium and other elements in treated material that commonly exceed 0-5 ppm.
7) Ability to vary spot size from 5-100 microns in diameter.

The benefits of these techniques include:
   a) No substantial sample preparation
   b) Virtually non-destructive analysis of any material
   c) Quantitative assessment of minor and trace elements
   d) High speed, non-contact analysis
   e) Depth profiling of layered structures and surface coatings
   f) Simple methodology
   g) Cost per analysis time: 1-10 samples per second (on a single stone or reference) are achievable
   h) Portability of the LIBS system.
   i) Broadband, full spectrum analysis 200-900 nm or tailored to specific wavelength ranges (using commercially available spectrometers and ancillary equipment).
   j) Lasers used in both these systems are solid state and do not exhibit the potential dangers of Excimer Lasers and the related toxic gas problems.

These systems typically employ a 10-200 micron ablation area, and have the capacity to ablate from millimeters to microns. As noted above, it is possible to control the analysis system in conjunction with a microinscription system. Likewise, known techniques of laser drilling of gems as part of a treatment process may also be performed.

Various statistical algorithms, such as PCA (Principle Component Analysis), may be employed in the data analysis.

The preferred lasers have emission in the UV range includes 266 nm, 213 nm and 193 nm. Cetac has a triplet device using OPO (Optical Parametric Oscillator) designated LSX-3000 and yields all three wavelength ranges. Thus, the laser may have a primary output or harmonically modified output in the UV range. Other types of lasers may also be employed. The energy levels that had been used for analyzing gems in ICP-MS range from 2 mJ to 170 mJ, and it is believed that a similar range of power output would be appropriate for LIBS and LA-ICP/AES-OES analysis of gemstones and minerals. The laser is typically focused through a microscope or similar optical system to provide smaller spot size and lower actual damage to gem materials. For example, a focused 213 nm laser can achieve a spot size of 5-10 microns.

213 nm lasers are particularly advantageous, since these provide good coupling efficiency in UV transmissive materials such as gemstone. The New Wave UP 213 System advantageously provides viewing optics with an 8× objective. Various sample gases may be employed. For example, argon or helium may be used, with higher sensitivity generally available when using helium as a sample cell gas. The Cetac-LSX 3000 delivers 193 nm wavelengths with a much shorter pulse width than any excimer system. Combined with the powerful 193 nm output for microanalysis of the most difficult materials, the LSX 3000 also can deliver high-energy 266 and 213 nm output to the sample all from a single compact platform.

Up to 10 spectrometers can be chained together or used individually depending on the area of the spectrum of interest. Advantageously, spectrometric features are selected for analysis based on the trace element(s) of interest, using a minimum number of spectrometers.

The base of each ablated laser crater can be scanned at elevated magnifications and used as confirmation of the identifying laboratory issuing the report. This pattern can be used to confirm that a specific laboratory issued the supporting report. Thus, since the microscopic structure of the laser ablation pattern for a single spot is non-deterministic, it serves as a fingerprint for the stone, and may be recorded for authentication purposes.

It is therefore an object of the invention to provide a system for analyzing chemical composition of a sample, comprising applying a material to a surface of the sample, containing a reference element; a system for generating focused energy beam for exciting a sample at a surface representing the elemental composition thereof; a spectrometer for determining atomic emission characteristics from the sample; and processor for receiving an output from the spectrometer, analyzing said output to determine atomic composition, said processor automatically comparing said output with data within a database derived from exemplars and extracting a signal relating to said reference element.

The processor may communicate with a database containing records representing a plurality of spectrometer outputs each representing a different analysis of a respective sample and/or execute an algorithm for predicting a treatment transformation of a sample.

The system may further comprise a set of physical exemplars for standardizing readings from said spectrometer, for example to calibrate or standardize the system.

The system is preferably self-contained and portable, including a sample mount, the laser and the said spectrometer.

Advantageously, the laser and spectrometer are part of a LIBS and/or LA-ICP/AES-OES, and possibly a combined instrument.

According to a preferred embodiment of the invention, a sample positioning system is provided, adapted to hold and position a gemological sample. The sample positioning system may automatically reposition the gemological sample between sequential excitations.

The system may be used in conjunction with a reference sample comprising a mineral having a predetermined trace element composition. References samples and the corresponding samples for analysis, may include corundum, beryl, chrysoberyl, diamond, tourmaline, quartz, garnet, opal, pearl, peridot, zosite, topaz, turquoise, zircon, amber, ivory, turtle or tortoise shell, jet, horn, mollusk shell, pearl, bone, and coral, or alternative materials used for the purpose of adornment or collection/display.

It is a further object according to the present invention to provide a kit of calibration samples, comprising at least four corundum samples, each having a predetermined and differing set of concentrations of at least two trace elements selected from the group consisting of Beryllium (Be), Lithium (Li), Magnesium (Mg) and Potassium (K). A calibration sample has, for example, a predetermined varying concentration of at least one of Beryllium (Be), Lithium (Li), Magnesium (Mg) and Potassium (K), with position along the form. A kit of calibration samples may also be provided, each sample comprising a corundum form, wherein each respective form has a predetermined varying concentration of a different one of Beryllium (Be), Lithium (Li), Magnesium (Mg) and Potassium (K), with position along the form.

A calibration sample may also take the form of a thin film, the thin film itself having a trace element, or having a coating with the trace element. The thin film may also be deposited on the sample for simultaneous testing of the test sample and reading of the calibration sample, for example by ablating through the thin film or taking measurements at, and adjacent to, the thin film.

It is another object of the invention to provide a method for analyzing a chemical composition of a sample, comprising exciting a sample to produce characteristic atomic emissions from elements therein; determining atomic emission characteristics from the excited sample; and analyzing the determined atomic emission characteristics to determine atomic composition of the sample, to predict at least one of (i) an origin of the sample, (ii) a treatment applied to said sample, and (iii) a feedback signal for controlling a process. The method may further comprise the steps of acquiring a set of reference spectra from objects having known properties, storing said reference spectra or information derived therefrom in conjunction with said known properties, and analyzing said determined atomic emission characteristics with respect to said stored reference spectra or information derived therefrom to predict a property of said sample.

The analyzing step of the method is preferably sensitive to concentrations of less than about 10 ppm of at least one of Beryllium (Be), Lithium (Li), Magnesium (Mg) and Potassium (K) in a corundum sample.

Advantageously, a laser absorptive target may be provided on the sample, wherein the exciting step comprises focusing a laser at said target. The target may be, for example a dye, pigment or film, and may include a reference element which is either related or identical to an element to be assayed, or distinct therefrom.

A mineral specimen may be provided as the sample, for example being used to compare an unknown to a known sample.

According to a preferred embodiment of the invention, the system is portable and self contained. For example, an energy beam generator is provided which draws power from a self-contained battery power source. Of course, the other elements of the system, which may include a controller, sample positioning system, and spectrometer, are also preferably self contained, portable, and powered by a battery, allowing the instrument to be readily used in the field.

The system preferably has a sample positioning system capable of positioning the sample along at least 5 axes of movement, which may be automated to present a desired portion of the surface of the sample for excitation.

DETAILED DESCRIPTION OF THE PREFERRED EMBODIMENT

Figure 1:
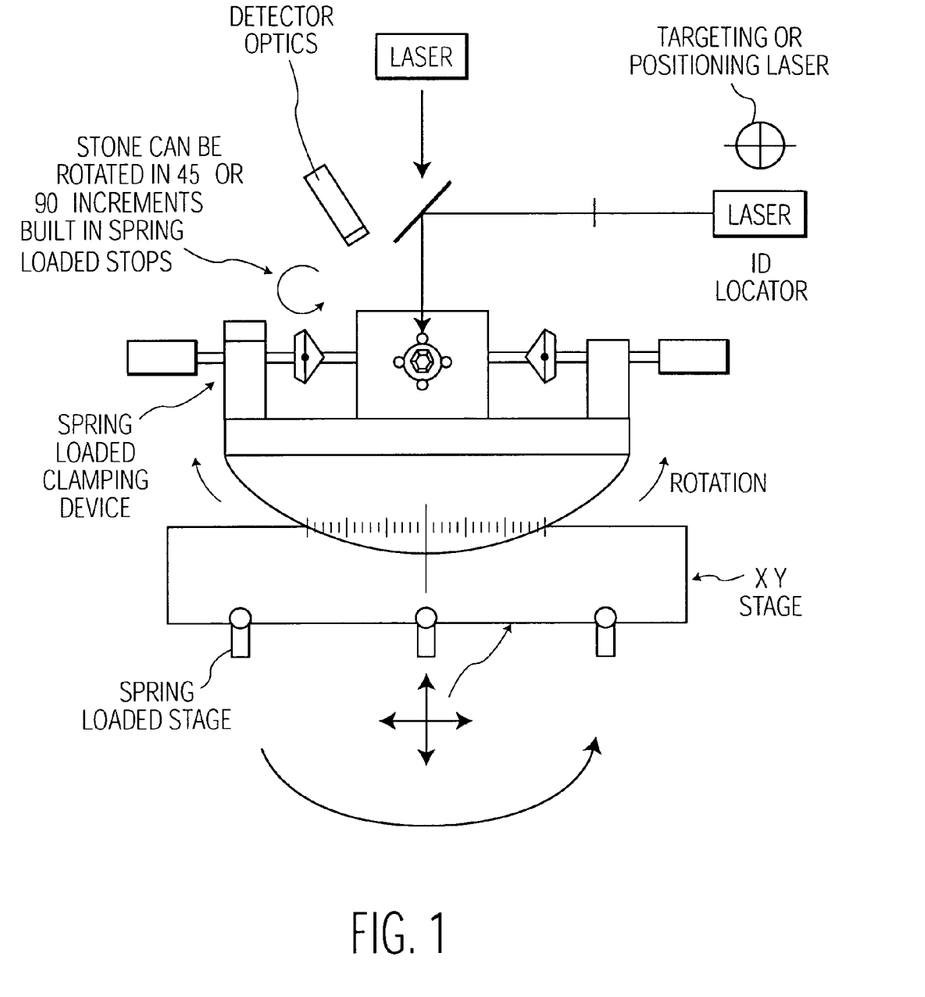
FIG. 1 shows a gemstone holding mechanism suitable for use in analyzing corundum gems according to the present invention

The system may employ a semi-automated sampling device for positioning material in the laser beam at optimum signal angle, as shown in FIG. 1.

"Sticky tack" may also be used as a medium to hold samples in place. Gem sizes down to approximately 2 mm have been effectively analyzed using LA-ICP/OES-AES. LIBS might also be applied to analyze stones of about 2 mm. Accordingly, a small container may be filled with sticky tack, mounted on an XYZ stage with radius tilting capability. The stage is adjusted for position and angle with respect to the laser.

However, the sample holder and analysis chamber shown in FIG. 1 is a more mechanically controlled environment. Ideally, the ablating laser is directed to hit the target at approximately 90 degrees, producing an ideal, flat bottomed, ablated crater, rather than a conical shape or distorted depression. Grazing angles can potentially deflect the beam from the target area and yield erroneous results.

A positioning or targeting laser of the HeNe Type, generating a cross hair pattern, can be reflected to the sample with a 45 degree first surface, retractable mirror in order to establish correct alignment with the sample surface. A second mirror at a 45 degree angle in the positioning laser's path can generate a direct image of the target area.

The system may employ an auto-focus positioning system for one or all of the laser ablation focal point establishment, observation, and gross positioning functions. A video or electronic camera may be employed for observation of the process.

The holding device is a spring loaded, clamping mechanism that allows for various size gemstones. The supporting end of the holding clamp (cutlet end) is a fixed distance from the center post of the device. Each spring loaded clamp is capable of 360 degree rotation in 45 degree increments, locking into place with spring loaded ball stops. Multiple stones can be loaded around the center post. The entire assembly is mounted on an XYZ stage for flexibility in positioning. This entire mechanism is mounted on a circular base, which is designed to allow tilting of the entire stage and therefore the sample stone, so that ablation, if necessary, can be focused on the girdle, pavilion or crown facet areas, as required. The positioning mechanism may be manually operated or automated using servo or stepping motors and associated controls. An automated vision system may be used to control a fully automated positioning and sampling system, to reduce manual effort, increase throughput, and acquire a set of optimal samples for a relatively complete analysis of a stone.

The holding device is placed within a shrouded area or enclosure, and a helium or argon purge applied. The area is preferably optically shielded for laser-eye safety, and to reduce background light for the spectrometer.

The sample readings are obtained and analyzed in known manner, using typical instrumentation. Advantageously, the instrument, and in particular a LIBS-only embodiment, could be provided as a portable device, allowing field use and non-permanent installation.

There has thus been shown and described a novel system and method for analyzing a chemical composition of a sample, preferably a gemstone, to detect trace element composition, and a means for calibrating the detector using an efficient scheme, of which various embodiments may fulfill some or all of the objects and advantages sought therefore. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims.

REFERENCE APPENDIX

The following references, are expressly incorporated by reference in their entirety as if set forth explicitly herein:
THEMELIS, "Beryllium-Treated Rubies & Sapphires"
THEMELIS, "Flux-Enhanced Rubies & Sapphires"
Periodic Table Atomic Properties of the Elements
THOMPSON, "Building "Be"-tter? Sapphires"
Search for laser induced breakdown spectroscopy, www.overture.com/d/search/p/netzero/?Keywords=laser+induced+breakdown+spectr . . .
Be beryllium (French: glucinium)
New Text Documents
"Recent Developments in Instrumentation for Induced Breakdown Spectroscopy", www.dekker.com/servlet/product/DOI/101081ASR120004896
American Gemological Laboratories, Gem Identification Report, Doc. No. ID 13458
American Gemological Laboratories, Colored Stone Grading Report, Doc. No. CS 36463
American Gemological Laboratories, Colored Stone Origin Report, Doc. No. CS 36600
American Gemological Laboratories, Colored Stone Origin Report, Doc. No. CS 36762
Spinel
"Lab develops colorful beryllium detection technology", chemicals.wycn.net/images/dhaq.gif
PERETTI, ET AL., "Contributions to Gemology", No. 1 May 2002, www.gemresearch.ch/journal/cover.htm
GILCHRIST, ET AL., "Spectroscopy: Mastering the Techniques"
Inductively Coupled Plasma-Mass Spectrometry (ICP-MS), Links for Mineralogists, www.uni-wuerzburg.de/mineralogie/links/tools/icp-ms.html
Chemical fingerprinting of some East African gem rubies by Laser Ablation ICP-MS
"Inductively Coupled Plasma Mass Spectrometry", www.soes.soton.ac.uk/research/groups/IGU/Icpms.htm
"Non destructive" Laser Ablation ICP-MS Investigations on Sapphires", ETH
"Chemical Identification Charts for Beryllium Treated Corundum", GRS
Test runs ICP/AES OES Spectro Analytical Instruments, Inc.
"Evaluation of gemstones by laser ablation—ICP-AES"
2004 Winter Conference on Plasma Spectrochemistry
Basic Overview of ICP-AES, www-odp.tamu.edu/publications/tnotes/tn29/technot2.htm
Spectro X-Lab X-L_engl.ppt
Spectro Ciros State of the Art CCD-ICP Technology for High Efficiency Analysis brochure
"Secondary Ion Mass Spectrometry (SIMS)", www.mri.psu.edu/mcl/techniques.sims.asp
"The Sputtering process", www.cascade.co.uk/thesims.htm
Desktop Mini SIMS, www.microphotonics.com/SIMS.html
An Introduction to Laser-Induced Breakdown Spectroscopy, LIBS Technique
The LIBS Technique, pearl1.lanl.gov/external/LIBS/technique.htm
LIBS2000+ Laser-induced Breakdown Spectrometer
MATTLEY, "Broadband LIBS Analysis of Related Bacillus Spores", Atomic Spectroscopy, February 2004
Laser-Induced Breakdown Spectroscopy (LIBS), www.imi.cnrc-nrc.gc.ca/english/HTML/Carrefour_d_informations/Factsheets/LIB S.htm
LIBS2000+ Broadband Spectrometer, www.oceanoptics.com/Products/LIBS.asp
PORTA-LIBS 2000, Introducing the first truly portable Laser Induced Breakdown Spectroscopy System, kigre.com/scientific.html
KOENIG, "Unique Solid-State Triple Wavelength Laser Ablation System for High Performance Analysis of Solids"
High Peak Power Compact Permanently Aligned MK-367 Nd:YAG Laser System for a Range of OEM Applications
EX5 Mini Excmer, GAM LASER, INC.
SpectronMini-Q Series Lamp Pumped Pulsed Nd:YAG Lasers, translate.google.com/translate?hl=en&sl=it&u=www.gsilumonics.com/product
HUGHES, "LIBS-A new beryllium testing method", www.palagems.com/beryllium_libs_testing.htm
"Laser Induced Plasma Spectroscopy", www.ws.chemie.tu-muenchen.de/laser/LIPS.htm
Pittcon 2004 Abstracts 17800-400, 17800-500, 17800-600
See also:
SIMS
www.cascade.co.uk/serv01.htm
www.asu.edu/clas/csss/SIMS/funds.html
www.chem.qmw.ac.uk/surfaces/scc/scat5_5.htm
fate.clu-in.org/graphite_main.asp
www.mee-inc.com/sims.html
www.yb.gmm.gu.se/method.php?ID=5
ND-YAG Laser
kigre.com/MK367data.pdf
www.quantel.fr/uk/scien/cfr.htm
www.bigskylaser.com/compactseries.html

What is claimed is:

1. A system for analyzing a chemical composition of a, gemstone comprising:
(a) applying a dye or pigment as a thin film having a consistent thickness to a surface of the gemstone, containing a reference analyte;
(b) a laser for generating a focused energy beam laser pulse for exciting the gemstone at a surface representing the elemental composition thereof to vaporize the reference analyte;
(c) a spectrometer for determining atomic emission characteristics from the sample; and (d) a processor for receiving an output from the spectrometer, analyzing said output to determine atomic composition, said processor automatically comparing said output with data within a database derived from exemplars and extracting a signal relating to said reference analyte.

2. The system according to claim 1, wherein said processor communicates with a database containing records representing a plurality of spectrometer outputs each representing a different analysis of a respective gemstone.

3. The system according to claim 1, wherein said processor executes an algorithm for predicting a treatment transformation of a gemstone.

4. The system according to claim 1, wherein said system further comprises a set of physical exemplars for standardizing readings from said spectrometer.

5. The system according to claim 1, wherein a sample mount, said laser and said spectrometer are together self-contained and portable.

6. The system according to claim 1, wherein said laser and said spectrometer are part of a LIBS.

7. The system according to claim 1, wherein said laser and said spectrometer are part of a LA-ICP/AES-OES.

8. The system according to claim 1, further comprising a gemstone positioning system, adapted to hold and position the gemstone.

9. The system according to claim 8, wherein said sample positioning system automatically repositions the gemstone between sequential excitations.

10. The system according to claim 1, in combination with a gemstone comprising a mineral having a predetermined trace element composition.

11. The system according to claim 1, in combination with a gemstone comprising corundum.

12. The system according to claim 1, in combination with a gemstone comprising beryl.

13. The system according to claim 1, in combination with a gemstone comprising chrysoberyl.

14. The system according to claim 1, in combination with a gemstone comprising at least one of diamond, tourmaline, quartz, garnet, opal, pearl, peridot, zosite, topaz, turquoise, and zircon.

15. A method for analyzing a chemical composition of a gemstone comprising:
(a) exciting a gemstone to produce characteristic atomic emissions from elements therein;
(b) determining atomic emission characteristics from the excited gemstone; and
(c) analyzing the determined atomic emission characteristics to determine atomic composition of the gemstone to predict at least one of (i) an origin of the gemstone, (ii) a treatment applied to said gemstone, and (iii) a feedback signal for controlling a process.

16. The method according to claim 15, wherein said analyzing step is sensitive to concentrations of less than about 10 ppm of at least one of Beryllium (Be), Lithium (Li), Magnesium (Mg) and Potassium (K) in a corundum sample.

17. The method according to claim 15, further comprising the step of providing a laser absorptive target on said sample, wherein said exciting step comprises focusing a laser at said target.

18. The method according to claim 15, further comprising the step of providing a mineral specimen as the sample.

19. The method according to claim 15, further comprising the steps of acquiring a set of reference spectra from objects having known properties, storing said reference spectra or information derived therefrom in conjunction with said known properties, and analyzing said determined atomic emission characteristics with respect to said stored reference spectra or information derived therefrom to predict a property of said sample.

20. The method according to claim 15, wherein said exciting step comprises powering an energy beam generator with a self-contained battery power source.

21. The method according to claim 15, further comprising providing a sample positioning system capable of positioning the sample along at least 5 axes of movement.

22. The method according to claim 15, further comprising providing a sample positioning system capable of automatically positioning the sample along at least 5 axes of movement to present a desired portion of the surface of the sample for excitation.

\* \* \* \* \*